(12) United States Patent
Kuo et al.

(10) Patent No.: US 8,871,721 B2
(45) Date of Patent: Oct. 28, 2014

(54) METHODS FOR INHIBITING PERITONEAL DISSEMINATION OF CANCER CELLS

(76) Inventors: Min-Liang Kuo, Taipei (TW); Been-Ren Lin, Taipei (TW); Cheng-Chi Chang, Taipei (TW); Chiung-Nine Chen, Taipei (TW)

(*) Notice: Subject to any disclaimer, the term of this patent is extended or adjusted under 35 U.S.C. 154(b) by 226 days.

(21) Appl. No.: 13/409,325

(22) Filed: Mar. 1, 2012

(65) Prior Publication Data
US 2012/0165253 A1 Jun. 28, 2012

Related U.S. Application Data

(63) Continuation of application No. 12/220,332, filed on Jul. 23, 2008.

(51) Int. Cl.
- *A61K 38/18* (2006.01)
- *A61P 35/00* (2006.01)
- *G01N 33/574* (2006.01)
- *G01N 33/50* (2006.01)

(52) U.S. Cl.
CPC .... *G01N 33/57419* (2013.01); *G01N 33/57449* (2013.01); *G01N 2800/54* (2013.01); *G01N 2333/475* (2013.01); *G01N 2800/50* (2013.01); *G01N 33/5011* (2013.01); *A61K 38/18* (2013.01); *G01N 33/57446* (2013.01)
USPC ............................ 514/19.3; 514/7.6; 530/399

(58) Field of Classification Search
None
See application file for complete search history.

(56) References Cited

U.S. PATENT DOCUMENTS 7,214,480 B2 * 5/2007 Kuo et al. .................... 435/4

OTHER PUBLICATIONS

Gardini et al., Expression of connective tissue growth factor is a prognostic marker for patients with intrahepatic cholangiocarcinoma, Digestive and Liver Disease 37, 269-274, 2005.*
Chang et al., Effect of Connective Tissue Growth Factor on Hypoxia-Inducible Factor 1α Degradation and Tumor Angiogenesis, J. Natl. Cancer Inst. 98, 984-995, 2006.*
Koliopanos et al., Connective Tissue Growth Factor Gene Expression Alters Tumor Progression in Esophageal Cancer, World J. Surg. 26, 420-427, 2002.*
Lin et al., Connective Tissue Growth Factor Inhibits Metastasis and Acts as an Independent Prognostic Marker in Colorectal Cancer, Gastroenterology, 128, 9-23, 2005.*
Jacobi et al., Inhibition of Peritoneal Tumor Cell Growth and Implantation in Laparoscopic Surgery in a Rat Model, Am. J. Surg., 174, 359-363, 1997.*
Szeto et al., Connective Tissue Growth Factor Is Responsible for Transforming Growth Factor-Beta-Induced Peritoneal Mesothelial Cell Apoptosis, Nephron Exp. Nephrology, 103, e166-e174, 2006.*
Chambers et al., Dissemination and growth of cancer cells in metastatic sites, Nature Rev. 2, 563-572, 2002.*
Uekita et al. "CUB-Domain-Containing Protein 1 Regulates Peritoneal Dissemination of Gastric Scirrhous Carcinoma", Am J Pathol. 172(6): 1729-1739, Jun. 2008).

* cited by examiner

*Primary Examiner* — Elly-Gerald Stoica
(74) *Attorney, Agent, or Firm* — Porzio, Bromberg & Newman, P.C.

(57) ABSTRACT

A pharmaceutical composition for treating or preventing peritoneal dissemination is provided. The pharmaceutical composition includes an effective dose of connective tissue growth factor (CTGF) and a pharmaceutically acceptable carrier thereof.

16 Claims, 13 Drawing Sheets
(3 of 13 Drawing Sheet(s) Filed in Color)

SEQUENCE LISTING

<160> NUMBER OF SEQ ID NOS: 10

<210> SEQ ID NO 1
<211> LENGTH: 23
<212> TYPE: DNA
<213> ORGANISM: Homo sapiens
<220> FEATURE:
<223> OTHER INFORMATION: Human CTGF sense specific sequence

```
<400> SEQUENCE: 1
gcttaccgac tggaagacac gtt                                              23

<210> SEQ ID NO 2
<211> LENGTH: 22
<212> TYPE: DNA
<213> ORGANISM: Homo sapiens
<220> FEATURE:
<223> OTHER INFORMATION: Human CTGF antisense specific sequence

<400> SEQUENCE: 2
tcatgccatg tctccgtaca tc                                               22

<210> SEQ ID NO 3
<211> LENGTH: 22
<212> TYPE: DNA
<213> ORGANISM: Homo sapiens
<220> FEATURE:
<223> OTHER INFORMATION: Human Cyr61 sense specific sequence

<400> SEQUENCE: 3
cgaggtggag ttgacgagaa ac                                               22

<210> SEQ ID NO 4
<211> LENGTH: 24
<212> TYPE: DNA
<213> ORGANISM: Homo sapiens
<220> FEATURE:
<223> OTHER INFORMATION: Human Cyr61 antisense specific sequence

<400> SEQUENCE: 4
aggactggat catcatgacg ttct                                             24

<210> SEQ ID NO 5
<211> LENGTH: 20
<212> TYPE: DNA
<213> ORGANISM: Homo sapiens
<220> FEATURE:
<223> OTHER INFORMATION: Human DAPK sense specific sequence

<400> SEQUENCE: 5
ccagcagcag gcagcacttg                                                  20

<210> SEQ ID NO 6
<211> LENGTH: 20
<212> TYPE: DNA
<213> ORGANISM: Homo sapiens
<220> FEATURE:
<223> OTHER INFORMATION: Human DAPK antisense specific sequence

<400> SEQUENCE: 6
cacgggcgct gcaccactac                                                  20

<210> SEQ ID NO 7
<211> LENGTH: 20
<212> TYPE: DNA
<213> ORGANISM: Homo sapiens
<220> FEATURE:
<223> OTHER INFORMATION: Human Beta-actin sense specific sequence

<400> SEQUENCE: 7
gatgatgata tcgccgcgct                                                  20

<210> SEQ ID NO 8
<211> LENGTH: 20
```

```
-continued

<212> TYPE: DNA
<213> ORGANISM: Homo sapiens
<220> FEATURE:
<223> OTHER INFORMATION: Human Beta-actin antisense specific sequence

<400> SEQUENCE: 8
tgggtcatct tctcgcggtt                                                    20

<210> SEQ ID NO 9
<211> LENGTH: 19
<212> TYPE: DNA
<213> ORGANISM: Homo sapiens
<220> FEATURE:
<223> OTHER INFORMATION: Human CTGF PCR sense specific sequence

<400> SEQUENCE: 9
atgaccgccg ccagtatgg                                                     19

<210> SEQ ID NO 10
<211> LENGTH: 24
<212> TYPE: DNA
<213> ORGANISM: Homo sapiens
<220> FEATURE:
<223> OTHER INFORMATION: Human CTGF PCR antisense specific sequence
<300> PUBLICATION INFORMATION:
<308> DATABASE ACCESSION NUMBER: NM_001901
<309> DATABASE ENTRY DATE: 2009-10-05
<313> RELEVANT RESIDUES IN SEQ ID NO: (1243)..(1266)

<400> SEQUENCE: 10
tcatgccatg tctccgtaca tctt                                               24
```

METHODS FOR INHIBITING PERITONEAL DISSEMINATION OF CANCER CELLS

CROSS REFERENCE TO RELATED APPLICATION

This application is a continuation of U.S. patent application Ser. No. 12/220,332 filed Jul. 23, 2008, the disclosure of which application is hereby incorporated by reference into this application.

FIELD OF THE INVENTION

The present invention relates to a pharmaceutical composition. In particular, the present invention relates to a pharmaceutical composition for inhibiting peritoneal dissemination.

BACKGROUND OF THE INVENTION

Peritoneal metastasis mostly originates from the tumors in the neighboring digestive system and organs, such as intestine, stomach, liver, pancreas, etc. Tumor cells accumulate and adhere abundantly on the peritoneum through blood or the lymph node after falling into peritoneal cavity, but do not invade other substantial organs (such as spleen, uterus and ovaries) directly. These tumor cells adhere on the surfaces of these organs, and will proliferate to invade these organs directly for a long time. This is a common phenomenon for cancers in the digestive tract of the peritoneal cavity. For instance, cancers include gastric cancer, small intestine cancer, colon cancer, rectal cancer, appendiceal cancer and pancreatic cancer. Certainly, there are few cancer cells originated from the peritoneum, and this situation is named primary peritoneal surface cancer.

Metastasis in the peritoneal cavity was deemed as an expression manner of the late-stage cancer in the past. Therefore, most of doctors in oncology only administrated an assistant or a remissive treatment, such as radiotherapy, anti-cancer chemotherapy and immunotherapy, etc. However, immunotherapy dose not yet have a concrete result acceptable for everybody. Most of patients appear the phenomena of ascites accumulation and intestinal obstruction, so as to lead to extreme pain and starvation.

If active treatment is not administrated, these patients diagnosed the peritoneal metastasis in the peritoneal cavity only have several months to live (average survival rate is 5 to 6 months). Among this, colorectal peritoneal carcinomatosis is deemed as a disease treated with relaxation therapy before death.

In the past decade, some new therapies, including active cyto-reductive surgery combining with hyperthermic intraperitoneal chemotherapy, have shown that these therapies can improve the average post-operative survival rate to 32.4 months (Glehen et al., J. Clin. Oncol., 2004). This strategy seems to bring a hope to the late-stage cancer patients with peritoneal metastasis. However, with regard to the researches of the active cyto-reductive surgery supplemented with hyperthermic intraperitoneal chemotherapy, more than 50% researches are still shown that the post-operative mortality of this strategy is 5% high (Glehen et al., Lancet Oncol., 2004; Koppe et al., 2006; Yan et al., 2006), and the incidence is ranged between 25% and 35% (Glehen et al., J. Clin. Oncol., 2004; Glehen et al., Lancet Oncol., 2004; Koppe et al., 2006; Yan et al., 2006; Verwaal et al., 2003; Glehen et al., 2003). This strategy only has effect on the early-stage cancer patients. Therefore, researching the mechanism of peritoneal metastasis and developing new therapies are urgently needed to the late-stage cancer patients with peritoneal metastasis.

In the progress of the peritoneal cavity cancer patients (including colorectal cancer, gastric cancer and ovary cancer, etc.), in order to absorb more nutrients, cancer cells usually proceed the peritoneal metastasis. At this time, cancer cells must adhere and invade the mesothelial layer, proliferate and begin angiogenesis. Therefore, the behavior that cancer cells adhere on the surface of peritoneum can be deemed as the key point in the beginning of peritoneal metastasis.

The adhesion ability of cancer cells can be regulated by the amount of connective tissue growth factor (CTGF). CTGF is an extracellular matrix-associated molecule (Rocnik et al., 2006; Bornstein et al., 2000; Bornstein et al., 2002), and CTGF has been proved to influence various important cellular functions, such as regulation of mitosis, apoptosis, generation of extracellular matrix, angiogenesis and metastasis (Lau et al., 1999; Bork et al., 1993; Moussad et al., 2000; Brigstock et al., 1999; Perbal 2001; Babic et al., 1999; Planque et al., 2003). Recently, many researches are also shown that CTGF can enhance the adhesion of different normal cells, such as fibroblasts, platelets, endothelia cells and rat hepatic stellate cells (Babic et al., 1999; Gao et al., 2004; Chen et al., 2001; Jedsadayanmata et al., 1999). However, the regulation mechanism of CTGF adhering to cancer cells are not completely clarified.

Taiwanese Patent No. 1282419 has been disclosed that the amount of CTGF represents the inverse correlation with the possibility of invasion or metastasis in the lung cancer patients. U.S. Patent Application No. 2005/0147986 is further disclosed that the truncation of the constructed CTGF plasmid is performed to identify the active fragment of CTGF, and is further founded that the inhibition effect of the C-terminal (CT) domain-lacked CTGF to the cancer cells will decrease enormously.

Therefore, in order to clarify whether CTGF can change the activity of peritoneal dissemination of cancer cells, the possible regulation mechanism of CTGF to the cancer cell adhesion is further researched in the present invention. Furthermore, the possible relationship between CTGF and peritoneal metastasis recurrence is further researched in the present invention.

It is therefore attempted by the applicant to deal with the above situation encountered in the prior art.

SUMMARY OF THE INVENTION

The issue that CTGF can inhibit cancer cells to adhere on the peritoneal tissue and further decreases the occurrence of peritoneal metastasis and peritoneal carcinoma recurrence is firstly provided in the present invention.

Therefore, a pharmaceutical composition having one of functions of treating peritoneal dissemination and preventing peritoneal dissemination is provided. The pharmaceutical composition includes at least one of CTGF and an active fragment thereof.

Preferably, the at least one of CTGF and the active fragment thereof inhibits at least one matter selected from the group consisting of a cancer cell adhering to a peritoneal cavity, a formation of a peritoneal nodule and an activity of a trigger of an immune response.

Preferably, CTGF is a recombinant CTGF, and the active fragment of CTGF is one selected from the group consisting of a C-terminal (CT) domain, a mutant of CT domain, an active fragment of the recombinant CTGF and a recombination thereof.

Preferably, peritoneal dissemination is caused by a cancer selected from the group consisting of colon cancer, gastric cancer, ovary cancer and a combination thereof.

Preferably, the at least one of CTGF and the active fragment thereof forms an effective dose.

Preferably, the pharmaceutical composition further includes a pharmaceutically acceptable carrier.

In accordance with another aspect of the present invention, a pharmaceutical composition having one of functions of treating peritoneal carcinoma recurrence and preventing peritoneal carcinoma recurrence is provided. The pharmaceutical composition includes at least one of CTGF and an active fragment of CTGF. Preferably, peritoneal carcinoma recurrence is occurred after surgery, and the pharmaceutical composition further includes a pharmaceutical acceptable carrier.

In accordance with another aspect of the present invention, a method for screening a inhibitor of peritoneal dissemination is provided. The method includes steps of: (a) causing a compound to bind with a cell expressing CTGF; (b) measuring a first amount of an expression of the CTGF of the cell; and (c) determining whether the first amount is higher than a reference amount. The inhibitor inhibits a cancer cell adhering to a peritoneal tissue. Preferably, the cell is selected from a peritoneal tissue, and the reference amount is determined by a second amount of the expression of CTGF of the cell without being bound to the compound.

In accordance with another aspect of the present invention, a method for measuring a possibility of peritoneal dissemination being occurring to a patient is provided. The method includes steps of: (a) providing a peritoneal tissue from the patient; (b) measuring a first amount of an expression of CTGF of the peritoneal tissue; and (c) comparing the first amount with a reference amount. Preferably, the reference amount is determined by a second amount of the expression of CTGF of a normal peritoneal tissue. When the first amount of the expression of CTGF of the peritoneal tissue is higher than the reference amount, the compound has potential for positively regulating CTGF.

In accordance with another aspect of the present invention, a method for measuring a possibility of peritoneal carcinoma recurrence occurring to a patient is provided. The method includes steps of: (a) providing a peritoneal tissue from the patient; (b) measuring a first amount of an expression of CTGF; and (c) comparing the first amount with a reference amount. When a first amount is lower than the reference amount of CTGF of the normal peritoneal tissue, the cancer patient is deemed as in the high risk of peritoneal dissemination.

In accordance with another aspect of the present invention, a method for inhibiting peritoneal dissemination of a patient is provided. The method includes a step of providing the patient with at least one of CTGF and an active fragment of CTGF.

In accordance with another aspect of the present invention, a method for inhibiting peritoneal carcinoma recurrence of a patient is provided. The method includes a step of administering the patient with at least one of CTGF and an active fragment of CTGF.

The above objectives and advantages of the present invention will become more readily apparent to those ordinarily skilled in the art after reviewing the following detailed descriptions and accompanying drawings, in which:

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENT

Figure 1:
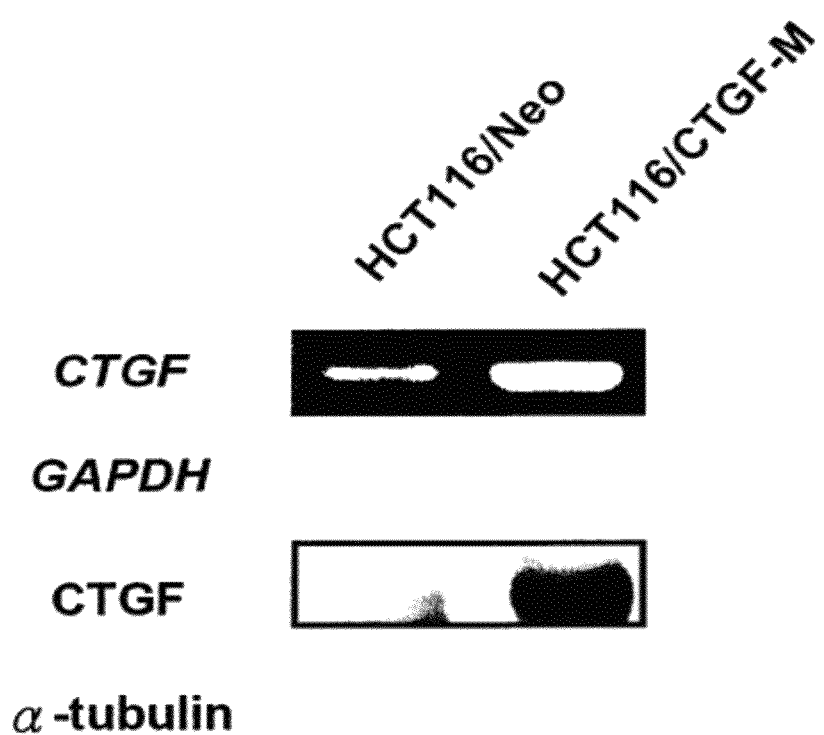
FIG. 1 is an electrophoresis diagram of CTGF mRNA and CTGF protein expression in HCT116/CTGF-M transfectant and HCT116/Neo cell line of the present invention.

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Pharmacological Experiments

1. Surgical Sampling and Immunohistological Staining
Subserosa (T3)- and perforating visceral peritoneum or peripheral organ (T4)-invasive colorectal cancer tissues from 136 consecutive patients were included at National Taiwan University Hospital during the period from December 1993 to July 1999. All patients underwent complete surgical resection, and their clinical and pathological data were available at the same time. Patients with histological proven peritoneal metastasis of colorectal cancer (CRC) diagnosed at the first presentation were defined as synchronous peritoneal seeding. All patients were followed up and this involved periodic examinations comprising serum blood-chemistry panels, carcinoembryonic antigen (CEA) level, endoscopy and abdominal ultrasonography and radiograms of the thorax. Patients with metachronous carcinomatosis were deemed to be clear of peritoneal disease at the initial curative colorectal resection, but subsequently became symptomatic on follow-up and were diagnosed with peritoneal recurrence on computed tomography or laparotomy. Immunohistological staining of CTGF was performed by the biotin-peroxidase complex using a polyclonal goat anti-human CTGF antibody (R&D Systems, MN). The pathologist assessing immunostaining intensity was blinded to patients' information and the results of immunohistological staining were classified using extent; these were level 0 (negative staining), level 1 (<5% of tumor cell stained), level 2 (<50% of tumor cells stained) and level 3 (>50% of tumor cells stained).

2. Incubation of Cells

The cell lines, HCT116, Coca-2 and LoVo, were incubated in the DMEM medium (Life Technologies, Inc.) supplemented with 4 mM L-glutamine and 10 mM sodium pyruvate. The medium of Coca-2 was further supplemented with 10 mg/ml of transferrin. HT29 cells were incubated in the RPMI 1640 medium (Life technologies, Inc.). All media were supplemented with 10% fetal bovine serum and 1% penicillin (10,000 U/ml)-streptomycin (10,000 U/ml) (Life Technologies, Inc.). All incubating conditions of these cell lines were controlled at 37° C. in the air with 5% $CO_2$. All cell lines should be refreshed the medium for every 2 to 3 days before fusion.

3. Recombination of CTGF

The Suspension FreeStyle™ 293-F cells (Invitrogen, San Diego, Calif.) were adopted to be the expression system. In accordance with the user's manual of FreeStyle 293-F expression system, the CTGF expression plasmid was transfected to the FreeStyle 293-F cell line, which then was incubated at 37° C. in the orbital shaker in the air with 8% $CO_2$ for 48 hours. The expression cells were microfiltrated and the diluted protein sample was concentrated. The recombinant protein was further separated speedy by Amicon Ultra-15 (Millipore Corp., Bedford, Mass.) so as to avoid the decrease of CTGF activity.

4. Western Blot Analysis

The abundantly-expressed cells were washed with phosphate buffered saline (PBS) containing 5 mM ethylenediaminetetraacetic acid (EDTA) and 1 mM sodium orthovanadate. The cell pellet then was suspended in the lysis buffer (containing 20 mM Tris-HCl (pH 8.0), 137 mM NaCl, 10% glycerol, 2 mM EDTA, 1% NP-40, 1 mM phenylmethylsulphonyl fluoride (PMSF), 20 µM leupeptin and 0.15 U/ml aprotinin) and was preserved on ice for 30 minutes. The tumor portions of CRC patients were also homogenized by the lysis buffer. The lysed cells were centrifuged at 4° C. in 14,500×g for 30 minutes, and the supernatant was collected. The protein in the supernatant was quantified by the spectrophotometer. After the electrophoresis was performed with 12% SDS-polyacrylamide gel, protein was transferred to a polyvinylidene difluoride (PVDF) membrane (Immobilon-P membrane, Millpore Corp., Bedford, Mass.). After the blot was blocked in a solution of 3% bovine serum albumin (BSA), 0.1% Tween 20 and PBS, the membrane-bound protein was probed with primary antibodies against β-actin (Sigma Chemical Co., St. Louis, Mo.), -catenin (BD Transduction Laboratories, BD Biosciences, Woburn, Mass.) or CTGF (R&D Systems, MN). The membrane was washed and then incubated with horseradish peroxidase (HRP)-conjugated secondary antibody (Santa Cruz Biotechnology, Santa Cruz, Calif.) for 30 minutes. The antibody-bound protein bands were detected with the enhanced chemical fluorescent reagent (Amersham Bioscience) and photographed with Kodak X-Omat Blue autoradiography film.

5. Preparation of CTGF Antibody

After the computed analysis, the amino acid fragment (aa243-263) of CTGF was adopted to synthesize the artificial peptide being the antigen for immunizing the rabbit. This amino acid fragment is similar with Fisp12 (mouse's CTGF) but different with Cyr61, Nov, WISP-1/Elm-1, WISP-2/rCop-1/CTGF-3 or WISP-3. The purification of CTGF antibody in the serum was processed in accordance with the literature published by Shimo et al (1999).

6. Analysis of Cell Attachment

Extracellular matrix (ECM)- or Matrigel-coated 24-well culture plate was adopted. Each well was coated 200 µl, and the culture plate was placed at 37° C. for 30 minutes. After $4 \times 10^3$ HCT116 cells were seeded in each well, the antibody was administrated so as to adhere on the well coated ECM or Metrigel. After incubating at 37° C. for 30 minutes, the wells were washed with 1× PBS twice, the attached cells were fixed with methanol and stained with crystal violet.

The excised rabbit peritoneum (about 1.6 centimeter square) was placed in a 6-well culture plate, then 1 ml of 1% BSA/RPMI 1640 medium was added in each well. Cells were labeled with the fluorescent substance, 1.77 mM 5-chloromethylfluorescein diacetate (CMFDA), at 37° C. for 30 minutes and then washed with 1% BSA/RPMI 1640 medium twice. The previous cellular supernatant ($2 \times 10^5$ cells per 1% BSA/RPMI 1640 medium, and a total of 0.5 ml) was covered on the peritoneum in the 6-well culture plate and incubated at 37° C. for 40 minutes. After washing gently with PBS, the cells adhered on the peritoneum were observed and counted under the fluorescence microscope (Olympus IX70; Olympus, Tokyo, Japan), which was qualified an NIBA filter (Ex=470 to 490 nm, and Em=515 to 550 nm) for observing CMFDA.

7. Reverse Transcription-Polymerase Chain Reaction (RT-PCR)

Reverse transcription of RNA isolated from cells was performed in a final reaction volume of 20 µl containing 5 µg total RNA in the First Strand Buffer with 10 mM dithiothreitol (DTT), 2.5 mM dNTP, 1 µg Oligo (dT) 12-18 primer and 200 unit/µl Moloney murine leukemia virus (MMLV) reverse transcriptase. The reaction was carried out at 37° C. for 2 hours, and was terminated by heating at 70° C. for 10 minutes. One microliter of the reaction mixture was then amplified by PCR using either of the following pairs of primers: (1) sense SEQ ID NO. 1 and antisense SEQ ID NO. 2, to produce a 500-bp fragment of the CTGF gene; (2) sense SEQ ID NO. 3 and antisense SEQ ID NO. 4, to produce a 450-bp fragment of the Cyr61 gene; (3) sense SEQ ID NO. 5 and antisense SEQ ID NO. 6, to produce a 420-bp fragment of the DAPK gene; and (4) sense SEQ ID NO. 7 and antisense SEQ ID NO. 8, to produce a 320-fragment of the -actin gene.

The PCR amplification was conducted in a reaction buffer containing 20 mM Tris-HCl (pH 8.4), 50 mM KCl, 1.5 mM $MgCl_2$, 167 µM dNTPs, 2.5 units of Taq DNA polymerase and 0.1 µtM primers. The reactions were performed in the Biometra Thermoblock (Biometra Inc., Florida, USA) using the following program: denaturing at 95° C. for 1 minute, annealing at 58° C. for 1 minute, and elongating at 72° C. for 1 minute, for a total of 23 cycles; the final extension took place at 72° C. for 10 minutes. Equal volumes of each PCR sample were subjected to electrophoresis in a 1% agarose gel, which was then stained with ethidium bromide and photographed under UV illumination.

8. Construction of CTGF Expression Plasmid

The cloning process of CTGF expression plasmid was described previously. Briefly, total RNA was extracted from the lung adenocarcinoma cell line, CL1-0, and CTGF cDNA was cloned and amplified by RT-PCR with the primers of SEQ ID NO. 9 and SEQ ID NO. 10 (PubMed Accession number: XM-037056), and subcloned into a pcDNA3/V5-His TOPO TA vector (Invitrogen, San Diego, Calif.) in the sense or the antisense direction. The CTGF expression plasmid was transiently or stably transfected into the colorectal cancer cell lines in vitro.

9. Stable Transfection Screening

Three microgram of the purified plasmid DNA was transfected into HCT116 cells and 3 µg AS-CTGF plasmid was transfected into HT29 cells by the TransFast™ transfection reagent (Promega, Madison, Wis.). After 24 hours of transfection, gentamycin (G418; Life Technologies, Inc.) was used to screen the stable transfectants. Thereafter, the selection medium was refleshed for every three days. After a two-week selection in G418, clones of resistant cells were isolated and allowed to proliferate in 100 µg/ml G418-containing medium. Integration of the transfected plasmid DNA was confirmed by RT-PCR and western blotting analysis.

10. Research of Colon Cancer Metastasis of Severe Combined Immunodeficiency (SCID) Mice HCT116 cells were harvested in 0.25% of trypsin-PBS-EDTA, washed with PBS and then resuspended in PBS at 1 million cells per 200 µl. One million HCT116 cells were injected intraperitoneally into 5 week-old female SCID mice, and the mice were divided into three groups.

Group I was the control group, and Group II was the co-treatment group. After injecting with HCT116 cells, mice in the Group I and Group II were immediately injected with the equal volumes of dimethyl sulfoxide (DMSO) and the recombinant CTGF (rCTGF, 1.5 mg/kg) respectively. Subsequently, the abovementioned step were continued once per two days for 14 days.

Group III was the post-treatment group. After the mice in the post-treatment group were injected with HCT116 cells for 3 days, rCTGF was injected therein every day for 7 days.

Mice were euthanized when they experienced a ~10% loss in body weight or if they appeared ill. Postmortem examinations included sectioning of kidney, lung, and liver that were stained with hematoxylin and eosin (H&E) followed by examination for tissue toxicity/damage by an experienced pathologist who was blinded to therapy.

11. Statistic Analysis

A comparison of the background data was carried out between the low-CTGF expression group and the high-CTGF expression group. The scale variables (expressed as mean±standard deviation) was proceeded by a Mann-Whitney test, and the nominal variables were proceeded by a Fisher's exact test. The analysis of the survival rate and recurrence data was done by the Kaplan-Meier method, and the Kaplan-Meier curves were compared by a log-rank test.

EXPERIMENTAL RESULTS

1. Suppression of Peritoneal Metastasis by CTGF in SCID Mice

It was hypothesized that CTGF, a metastasis-suppressor, in human colorectal cancer may act to cancer cell adhesion which is the key step of peritoneal metastasis in the present invention. To prove this hypothesis, the abundantly-CTGF-expressed HCT116/CTGF-M transfectant and HCT116/Neo cell line (the control group) for intra-abdominal cancer seeding were set up in the present invention.

Please refer to FIG. 1, which is an electrophoresis diagram of CTGF mRNA and CTGF protein expression in HCT116/CTGF-M transfectant and HCT116/Neo cell line of the present invention. From the result in FIG. 1, it was known that the CTGF-transfected HCT116/CTGF-M cell line really could abundantly express CTGF as comparing to HCT116/Neo cell line.

Figure 2:
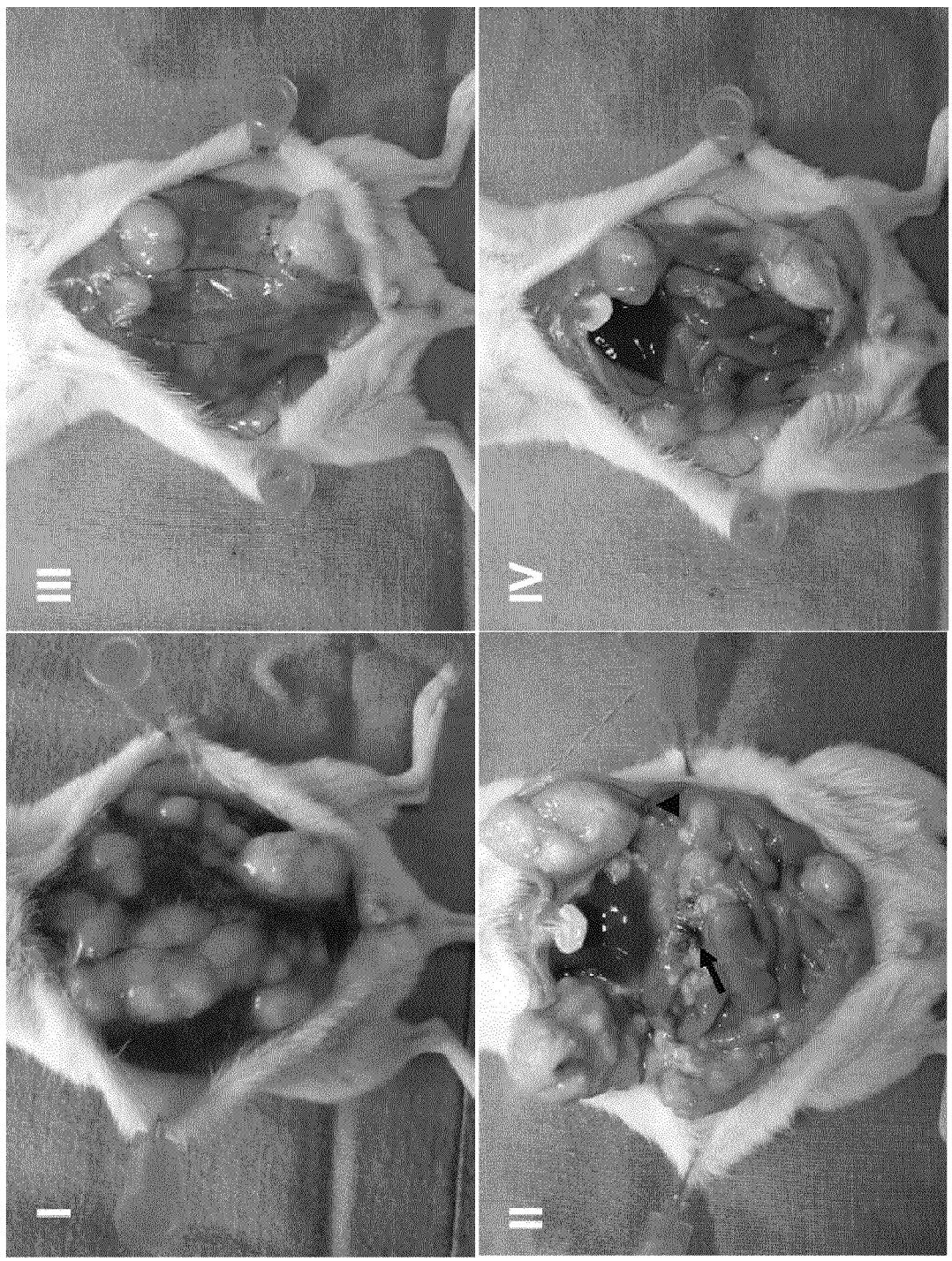
FIGS. 2-I to 2-IV are the peritoneal tumor distributions of dissection after injecting HCT116/CTGF-M and HCT116/Neo cell lines respectively into SCID mice for eight weeks.

Please refer to FIGS. 2-I to 2-IV, which are the peritoneal tumor distributions of dissection after injecting HCT116/CTGF-M and HCT116/Neo cell lines respectively into SCID mice for eight weeks. After injecting HCT116/CTGF-M and HCT116/Neo cell lines for five weeks (before dissection), the phenomenon that peritoneal tumor protrusion leads to the enlarged abdominal circumference was obvious (data not shown). In FIGS. 2-I and 2-II, HCT116/Neo transfectant was injected into the SCID mice, and the distributions of hemo-peritoneum and many nodules could be found after dissection. In FIGS. 2-III and 2-IV, HCT116/CTGF-M transfectant was injected into the SCID mice, and the phenomenon of hemo-peritoneum and the distribution of nodules were significantly decreased as comparing to the control group.

Table 1 is the result of peritoneal seeding of injecting HCT116/Neo and HCT116/CTGF-M transfectants respectively into SCID mice. Among this, the sample number of SCID mice was 10, and the diaphragm seeding distribution, the phenomenon of local bowel invasion and nodule number were determined respectively. The result in Table 1 is shown that the abundantly-expressed CTGF could substantially inhibit the diaphragm seeding distribution, bowel invasion and the number of tumor seeding.

TABLE 1

Results of peritoneal seeding of HCT116/Neo and HCT116/CTGF-M transfectants respectively in SCID mice

| | Peritoneal seeding | | | | | |
|---|---|---|---|---|---|---|
| | Diaphragm seeding[#] | | Local bowel invasion[#] | | Nodule count[&] | |
| | Involved No. | P-value | Involved No. | P-value | Median No. (range) | P-value |
| HCT116/Neo | 6/10 | 0.057 | 7/10 | 0.070 | 29 (23-38) | 0.0001 |
| HCT116/CTGF-M | 1/10 | | 2/10 | | 10 (7-13) | |

[#]Fisher's exact test;
[&]Mann-Whitney test

Figure 3:
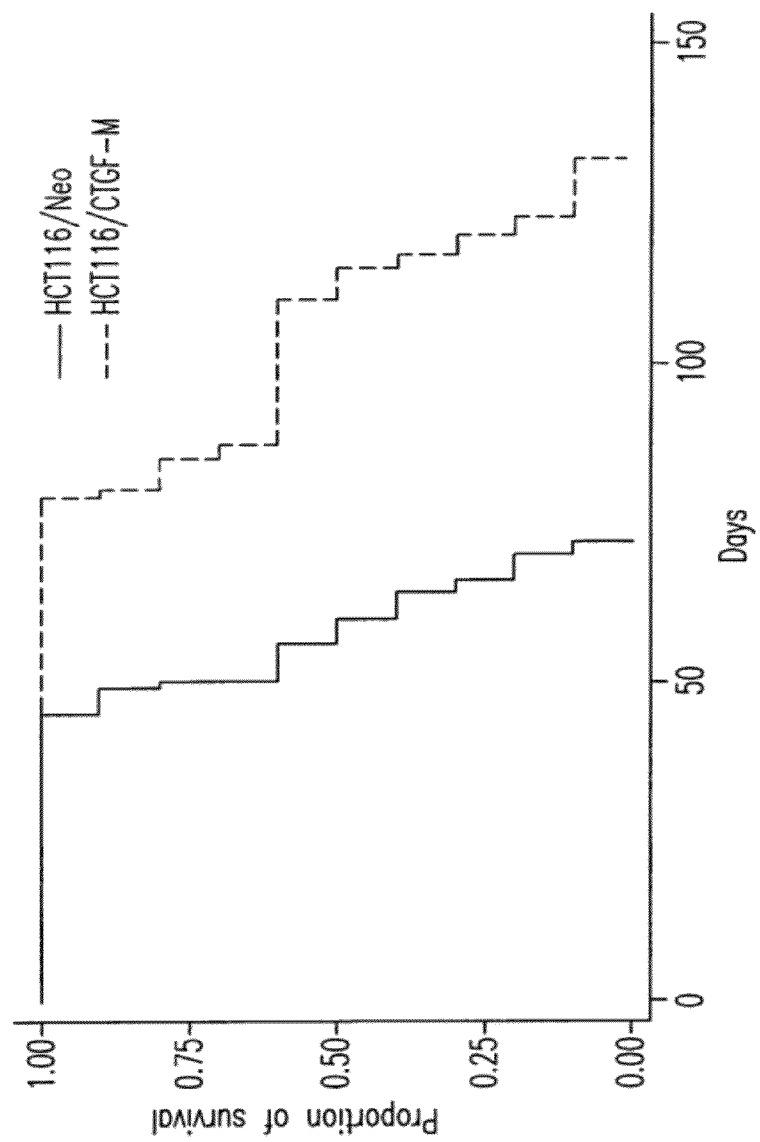
FIG. 3 is a relationship diagram showing the proportion of survival and time (days) after injecting HCT 116/Neo and HCT116/CTGF-M transfectants respectively to the SCID mice.

Please refer to FIG. 3, which is a relationship diagram showing the proportion of survival and time (days) after injecting HCT 116/Neo and HCT116/CTGF-M transfectants respectively to the SCID mice. From the result in FIG. 3, it could be found that the survival rate of the HCT116/CTGF-M-injected SCID mice was higher than that of the HCT116/Neo-injected SCID mice. The average survival days of the HCT116/CTGF-M-injected SCID mice were 58 days; however, the average survival days of the HCT116/CTGF-M-injected SCID mice were 81.8 days (p=0.001). Therefore, in accordance with the above-mentioned data, it was supposed that the abundantly-expressed CTGF could effectively inhibit the peritoneal dissemination progress of colorectal cancer, and the abundantly-expressed CTGF was beneficial in increasing the survival rate in vivo.

Subsequently, in order to research whether the growth of HCT116 colon cancer cells could be inhibited by rCTGF in the present invention, the mice were divided into three groups. The first group was the control group. After one million HCT116 cells were injected into the peritoneal cavity of female SCID mice, DMSO was injected thereinto for every two days for 14 days. The second group was the co-treatment group. After one million HCT116 cells were injected into the peritoneal cavity of female SCID mice, 1.5 mg/kg rCTGF was injected thereinto immediately (once per two days for 14 days), wherein the purpose of co-treatment group was mainly in simulating the direct intraoperative situation with free cancer cells on the peritoneal surface. The third group was the post-treatment group. After one million HCT116 cells were injected into the peritoneal cavity of female SCID mice, rCTGF was injected thereinto everyday from days 3 to 9, wherein the purpose of the post-treatment group was to simulate the clinical situation of the early-stage microscopic-transplanted surgery patients.

Figure 4:
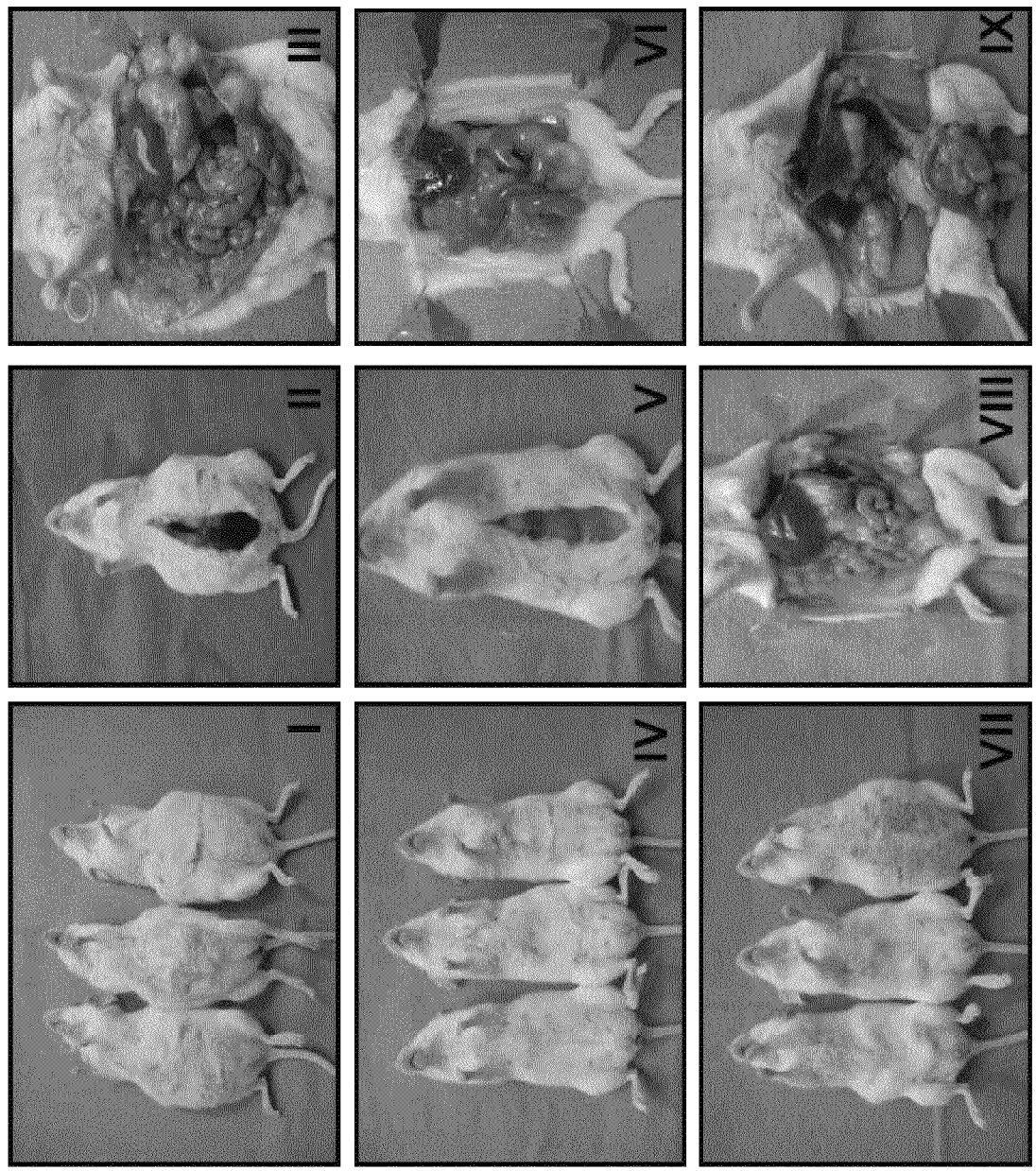
FIGS. 4-I to 4-IX are the dissection diagrams showing the effect of peritoneal dissemination while injecting rCTGF into the SCID mice in the control, co-treatment and post-treatment groups.

Please refer to FIGS. 4-I to 4-IX, which are the dissection diagrams showing the effect of peritoneal dissemination while injecting rCTGF into the SCID mice of control, co-treatment and post-treatment groups. In FIGS. 4-I to 4-III, all SCID mice were moribund within 40 days, and the increasing abdominal circumference was measured obviously. Bloody ascites were noted during dissecting the abdominal cavity and numerous peritoneal nodules were found. In the co-treatment (FIGS. 4-IV, 4-V and 4-VI) and the post-treatment (FIGS. 4-VII, 4-VIII and 4-IX) groups, the abdominal circumference of mice did not increase obviously, and the situations of the ascites and the peritoneal nodules in the peritoneal cavity were improved significantly after the mice in co-treatment group and the post-treatment groups were dissected as comparing to the control group, wherein the peritoneal cavities of three mice in the co-treatment group and one mouse in the post-treatment group did not have tumor dissemination (data not shown).

Figure 5A:
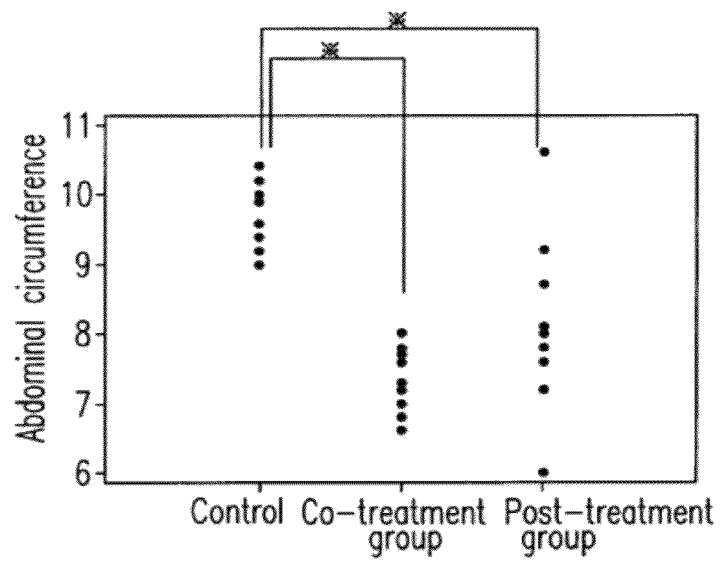
FIG. 5(A) is the quantitative result of the abdominal circumference of mice in the control, co-treatment and post-treatment groups.
Figure 5B:
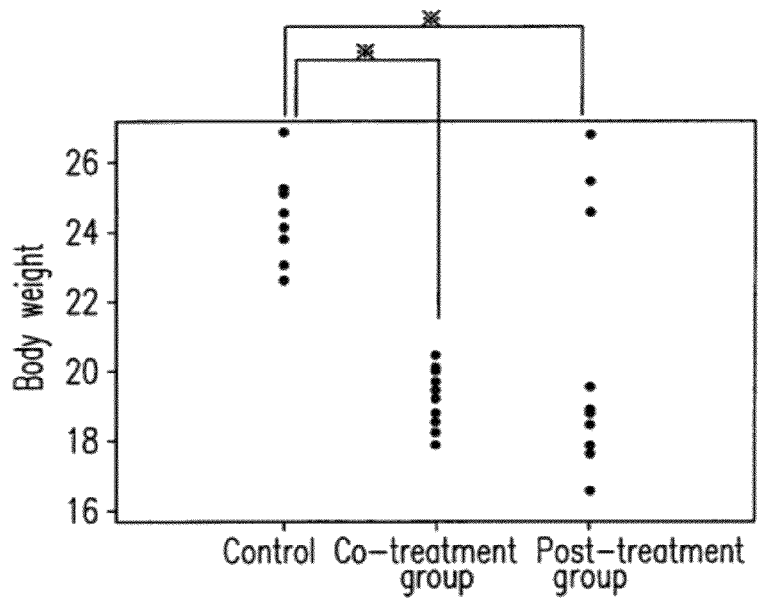
FIG. 5(B) is are the quantitative result of the body weight of mice in the control, co-treatment and post-treatment groups.

Please refer to FIGS. 5(A) and 5(B) respectively, which are the quantitative results of the abdominal circumference and body weight of mice in the control, co-treatment and post-treatment groups. The quantitative results in FIGS. 5(A) and 5(B) were corresponding to the results in FIGS. 4-I to 4-IX.

Figure 6:
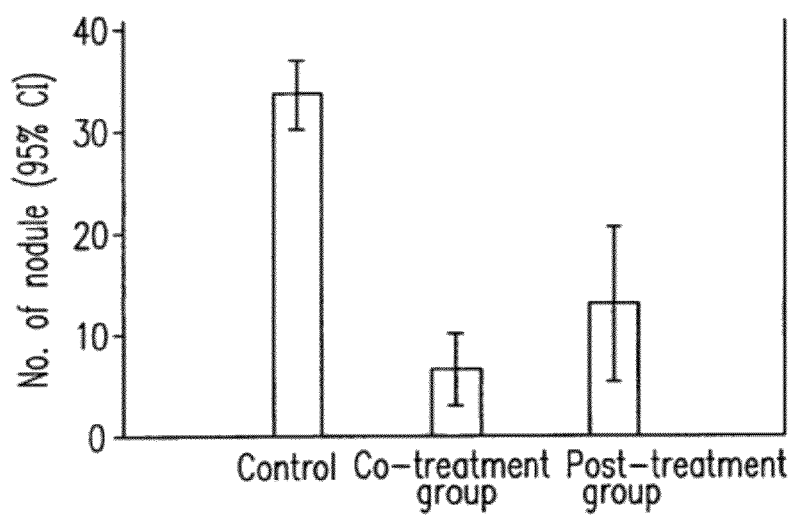
FIG. 6 is the quantitative result of peritoneal nodules of mice in the control, co-treatment and post-treatment groups.

Please refer to FIG. 6, which is the quantitative result of peritoneal nodules of mice in the control, co-treatment and post-treatment groups. The number of the peritoneal nodules in the mice were significantly decreased in the co-treatment and post-treatment groups as comparing to the control group.

In summary, the expression of CTGF indeed plays an important regulation role in the mechanism of peritoneal metastasis.

2. Inhibition of CTGF to Adhesion of Colon Cancer Cells

In order to clarify the playing role of CTGF in the adhesion of colon cancer cells, firstly, the expressions of CTGF in four different human colon carcinoma cell line (HCT116, LoVo, HT-29 and Caco-2) are determined by RT-PCR and Western blot.

Figure 7:
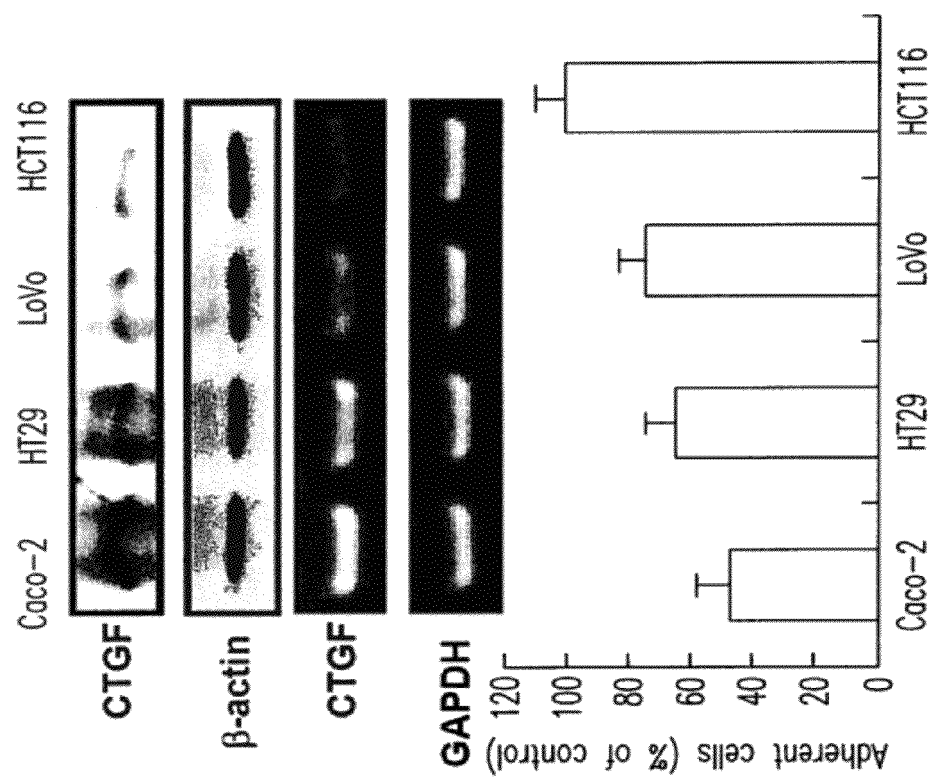
FIG. 7 is the expressions of CTGF mRNA and CTGF protein, and the cellular adhesion ability of CTGF in HCT116, LoVo, HT-29 and Caco-2 cell lines.

Please refer to FIG. 7, which is the expressions of CTGF mRNA and CTGF protein and the cellular adhesion ability of CTGF in HCT116, LoVo, HT-29 and Caco-2 cell lines. The result was shown that HCT116 cells had the lowest CTGF mRNA and protein expressions and the highest cellular adhesion ability. As comparing to Caco-2 cells, Caco-2 cells had the highest CTGF mRNA and protein expressions and the lowest cellular adhesion ability.

Figure 8:
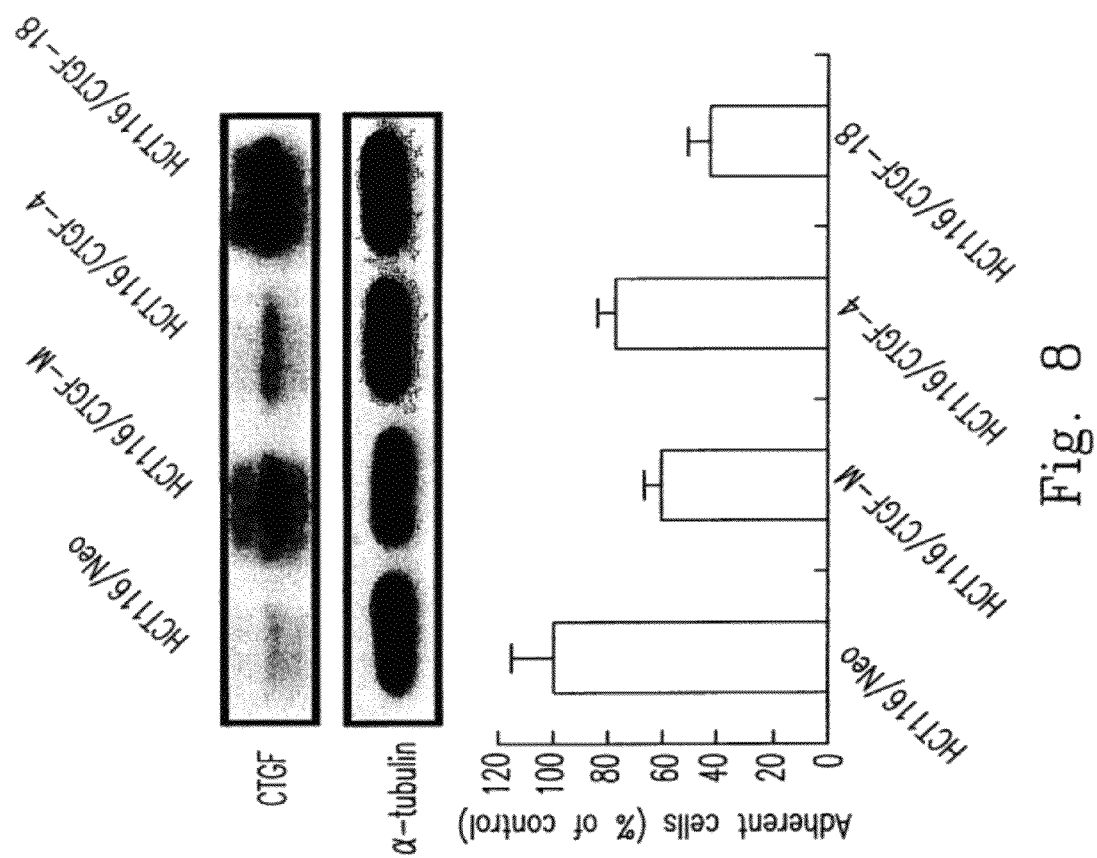
FIG. 8 is the CTGF expressions and the cellular adhesion abilities of HCT116/Neo, HCT116/CTGF-M, HCT116/CTGF-4 and HCT116/CTGF-18 transfectants.

The aforementioned experimental results using HCT116/Neo and HCT116/CTGF-M transfectants have been proved that the CTGF expression indeed have the effect to influence the peritoneal metastasis. Furthermore, the HCT116 transfectants (HCT116/CTGF-4 and HCT116/CTGF-18) with different CTGF expressions were screened in the present invention. Please refer to FIG. 8, which is the CTGF expressions and the cellular adhesion abilities of HCT116/Neo, HCT116/CTGF-M, HCT116/CTGF-4 and HCT116/CTGF-18 transfectants. Comparing with the control group (HCT116/Neo), the result was proved that CTGF expression represented the inverse correlation with the adhesion ability.

Figure 9:
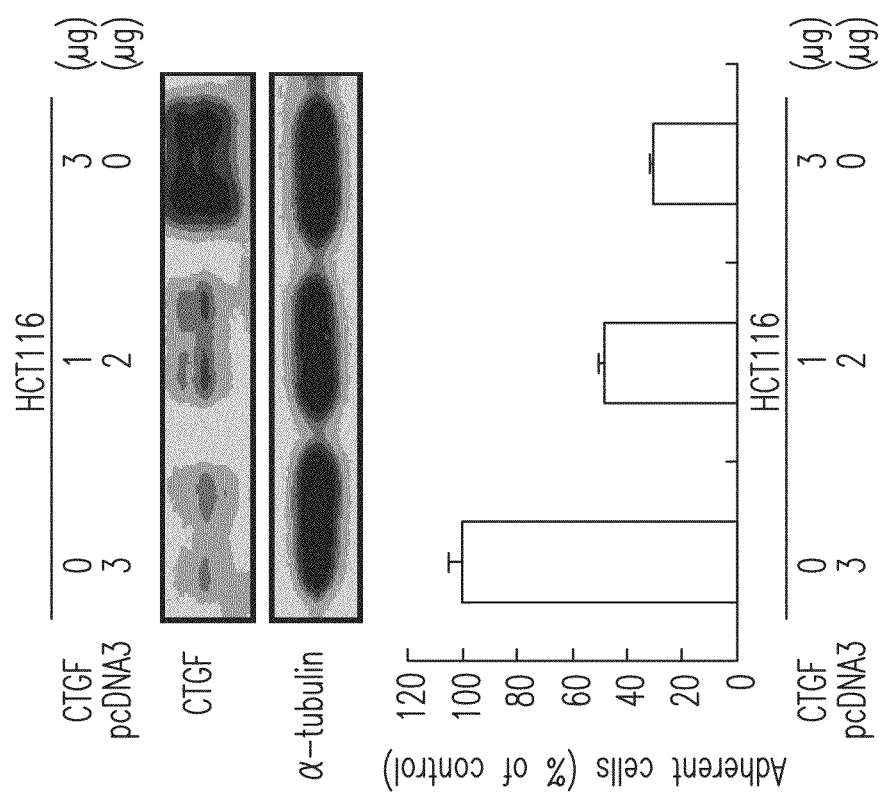
FIG. 9 is the influence of adhesion ability that different doses of the CTGF expression plasmid transiently transfect to HCT116 cells.

Please refer to FIG. 9, which is the influence of adhesion ability that different doses of the CTGF expression plasmid transiently transfects to HCT116 cells. The result was shown that different doses of CTGF would influence the adhesion ability of HCT116 cells. The higher CTGF dose made the worse adhesion ability, and the lower CTGF dose made the better adhesion ability.

Figure 10:
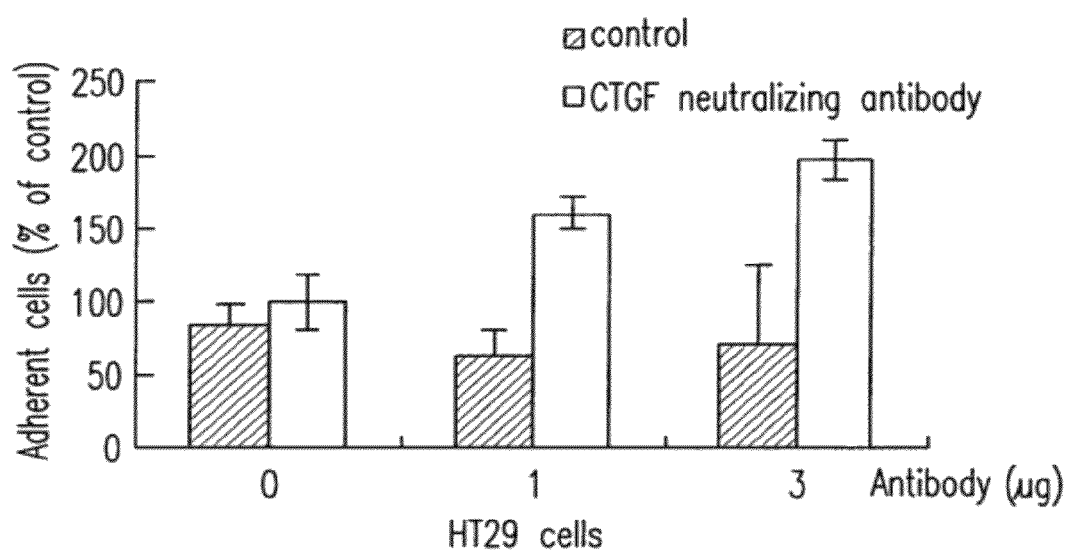
FIG. 10 is the function of different doses of CTGF neutralizing antibody antagonizing the stable CTGF expression in HT29 cell line.

Please refer to FIG. 10, which is the function of different doses of CTGF neutralizing antibody antagonizing the stable CTGF expression in HT29 cell line. The result was shown that the adhesion of HT29 cells would be significantly increased along with the doses (1 to 3 μg) of neutralizing antibody.

Figure 11:
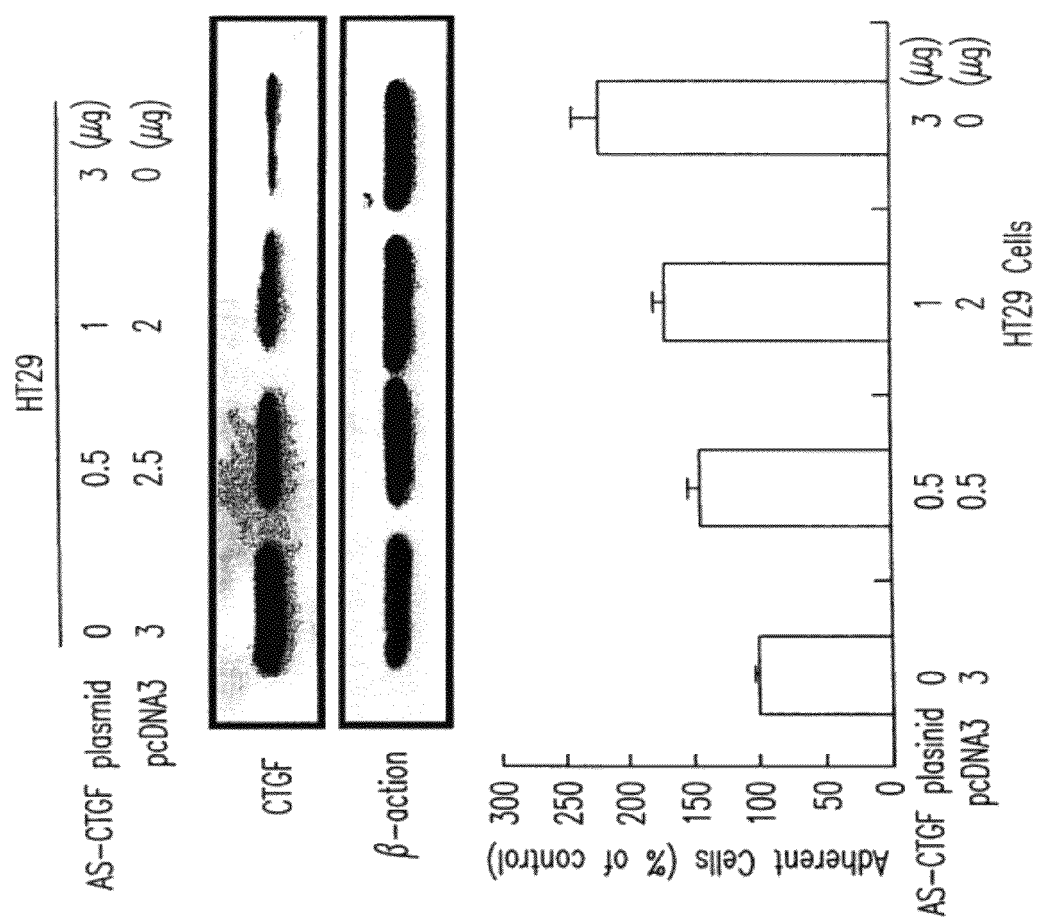
FIG. 11 is the CTGF expression and the CTGF adhesion ability of HT29 cell lines transfected with different doses of anti-sense CTGF plasmid.

Subsequently, the relationship between the CTGF expression and the cellular adhesion was discussed by transfecting with the antisense CTGF plasmid. Please refer to FIG. 11, which is the CTGF expression and the CTGF adhesion ability of HT29 cell lines transfected with different doses of anti-sense CTGF plasmid. The result was shown that the cells transfected with higher doses (0.5 to 3 μg) of anti-sense CTGF plasmid made the higher cellular adhesion.

3. CTGF Being a Predicted Marker of the Peritoneal Metastasis in Human's Colorectal Cancer (CRC)

The previous research (Lin et al., 2005) has been proved that the CTGF expression represents the inverse correlation with the lymph node metastasis of the colorectal cancer patients and the recurrence level of metastasis. Therefore, the possible relation between the CTGF contents of the primary tumor and the generated peritoneal carcinomatosis was further discussed in the present invention.

Figure 12:
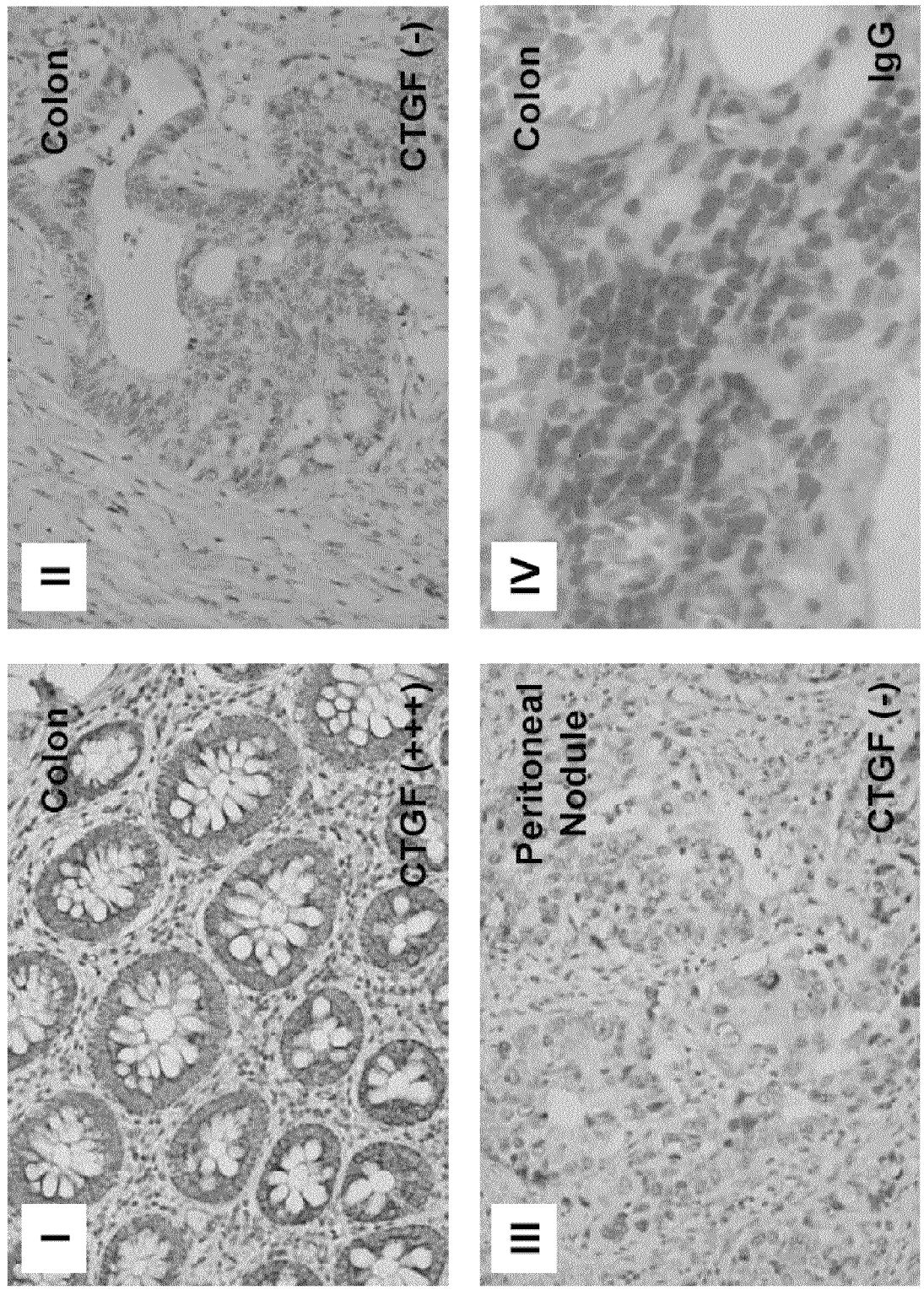
FIGS. 12-I to 12-IV are the most representative immunohistochemical staining in 136 colorectal cancer patient samples.

Please refer to FIGS. 12-I to 12-IV, which are the most representative immunohistochemical staining in 136 colorectal cancer patient samples. FIG. 12-I was the representative diagram of Level 3, which had a very high CTGF expression in the basal membrane and cytoplasm of the well-differentiated epidermoid carcinoma. FIGS. 12-II and 12-III were the representative diagrams of Level 0, and it could be found that the weak immune response existed in the poorly-differentiated colorectal cancer cells (FIG. 12-II) and their peritoneal dissemination nodules (FIG. 12-III). FIG. 12-IV was an immunohistochemical diagram of negative staining, which used IgG as the control group. Please refer to Table 2, which is the related pathological data of the clinical characteristics and CTGF expression diagrams of the immunohistochemical staining. In the analysis of 136 colorectal cancer patient samples, the low CTGF expression group occupied 55% (75/136) of the total samples and the high CTGF expression group occupied 45% (61/136) of the total samples.

TABLE 2

Clinical and pathological characteristics for high and low CTGF expression in T3 and T4 colorectal cancer (CRC)

| Feature | Number | CTGF expression Low | CTGF expression High | P-value |
|---|---|---|---|---|
| Patients | 136 | 75 | 61 | |
| Mean age (Year) | | 62.6 | 62.1 | 0.82 |
| Sex | | | | 0.618 |
| Male | 68 | 33 | 35 | |
| Female | 68 | 42 | 26 | |
| Tumor site | | | | 0.823 |
| Right | 45 | 23 | 22 | |
| Left | 44 | 25 | 19 | |
| Rectum | 47 | 27 | 20 | |
| Tumor Differentiation | | | | 0.007 |
| Poor | 26 | 21 | 5 | |
| Moderate | 106 | 52 | 54 | |
| Well | 4 | 2 | 2 | |
| Stage | | | | 0.040 |
| II | 47 | 20 | 27 | |
| III | 63 | 36 | 27 | |
| IV | 26 | 19 | 7 | |
| Lymph node | | | | 0.017 |
| N0 | 56 | 24 | 32 | |
| N1 | 43 | 24 | 19 | |
| N2 | 37 | 27 | 10 | |
| Intra-tumor invasion | | | | 0.301 |
| Present | 63 | 38 | 25 | |
| Absent | 73 | 37 | 36 | |
| CEA level (ng/ml) | | | | 0.582 |
| 3 | 44 | 23 | 21 | |
| >3 | 92 | 52 | 40 | |
| Synchronous peritoneal seeding | | | | 0.030 |
| Present | 35 | 25 | 10 | |
| Absent | 101 | 50 | 51 | |
| Metachronous peritoneal seeding | | | | 0.001 |
| Present | 21 | 17 | 4 | |
| Absent | 80 | 33 | 47 | |

In the low CTGF expression group, the CTGF expression had no significant relations with the age, sex, tumor location, pre-operative CEA content and intra-tumor invasion of the patients. In the high CTGF expression group, 16% (10/61) patients had synchronous peritoneal metastasis; however, 33% (25/75) patients had the phenomenon of synchronous peritoneal metastasis (p=0.030) in the low CTGF expression group.

From the result in Table 2, it could be known that the status of tumor differentiation, clinical level and lymph node metastasis significantly related to the CTGF expression. (p-values were 0.007, 0.040 and 0.017 respectively).

Figure 13:
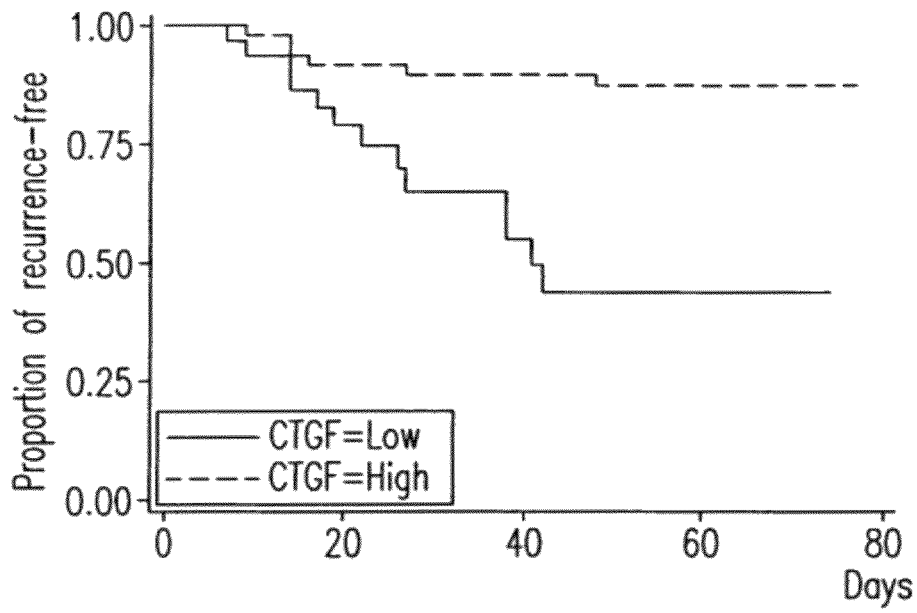
FIG. 13 is the relationship diagram showing time and the recurrence rate from post-operation to recurrence between the high CTGF expression group and the low CTGF expression group.
Figure 14:
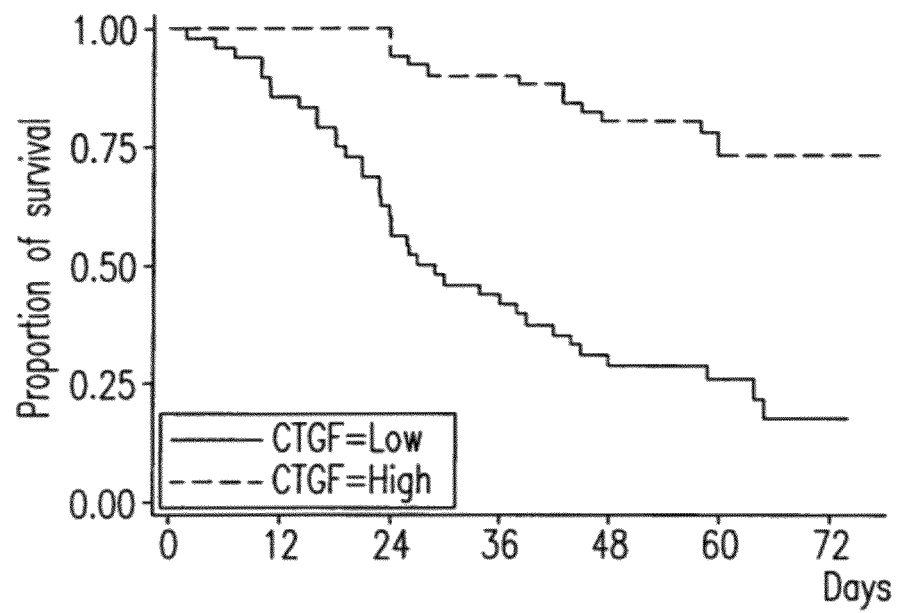
FIG. 14 is the relationship diagram showing time and the survival rate between the high CTGF expression group and the low CTGF expression group.

Furthermore, from the result in Table 2, it could be known that the patient samples without peritoneal metastasis diagnosed in the early surgery were 101, wherein 50 persons had low CTGF expression and 51 had high CTGF expression. The traces of the follow-up recurrence (FIG. 13) and survival rate (FIG. 14) were proceeded in accordance with this feature. From the comparison result in FIG. 13, it could be known that the time from post-operation to recurrence in the high CTGF expression group was significantly higher than that in the low CTGF expression group (p<0.001). From the result in FIG. 14, the significant difference (p<0.001) of the survival rate in the high and low CTGF expression patients could be known. Therefore, the above-mentioned clinical data have been proved that CTGF was the predictable marker of synchronous or non-synchronous peritoneal metastasis in the colorectal cancer patients.

In summary, adhesion ability of cancer cells on the peritoneum plays a considerable important key role in the peritoneal metastasis of the colorectal cancer. The present invention is first proved that CTGF not only can be the biomarker in predicting the recurrence of peritoneal metastasis, but also can be the another candidate therapy for the peritoneal cancer dissemination of the colorectal cancer patients.

In conclusion, the clinical data of immunohistological staining of the present invention have been proved that the probability of synchronous and non-synchronous peritoneal metastasis of the colorectal cancer which the lower CTGF content patients suffer is higher than that of which the higher CTGF content patients suffer. In addition, CTGF expressions in different colorectal cancer cell lines represents the inverse correlation with their adhesion ability, and the variances of CTGF expression affect the adhesion abilities of human colorectal cancer cell lines directly. Therefore, whether cancer patients possess the high risk of peritoneal metastasis is identified by determining the CTGF expression of primary colorectal cancer, and the phenomenon of peritoneal carcinomatosis of cancer patients is prevented and treated by administrating CTGF.

Furthermore, the abovementioned experimental results can be used in the present invention so as to provide a method for screening the inhibitor of peritoneal dissemination. First, a compound is bound with the cells expressing CTGF in the peritoneal tissue, and CTGF has inhibition ability of cancer cell adherence in the peritoneal tissue. Subsequently, the CTGF expression in the peritoneal tissue is determined. When the CTGF expression in the peritoneal tissue is higher than that in the cells without binding with the compound, the compound has potential for positively regulating CTGF.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for inhibiting a peritoneal dissemination of a cancer cell of a patient, the cancer cell being one selected from a group consisting of a gastric cancer, a small intestine cancer, a colon cancer, a rectal cancer, an ovary cancer, an appendiceal cancer and a pancreatic cancer, comprising a step of: administering to the patient an effective dose pharmaceutical composition, comprising a connective tissue growth factor (CTGF) and/or an active fragment thereof, wherein the CTGF and/or the active fragment thereof inhibits the cancer cell adhering to the peritoneal cavity or the formation of a peritoneal nodule, and the pharmaceutical composition is administered in one of two ways: once per two days for at least 14 days and once per day for at least 7 days.

2. The method according to claim 1, wherein the CTGF is a recombinant CTGF and/or the active fragment of CTGF is one selected from the group consisting of a C-terminal (CT) domain, a mutant of the CT domain, an active fragment of the recombinant CTGF and a combination thereof.

3. The method according to claim 1, wherein the patient is a mammal.

4. The method according to claim 3, wherein the mammal is one of a rodent and a human.

5. A method for inhibiting a peritoneal carcinoma recurrence after a treatment of a patient, comprising a step of: administering to the patient an effective dose pharmaceutical composition, comprising a connective tissue growth factor (CTGF) and/or an active fragment thereof, the CTGF and/or the active fragment thereof inhibits the cancer cell adhering to the peritoneal cavity or the formation of a peritoneal nodule, the treatment is a technique for treating the cancer cell, and is one selected from a group consisting of a radiation therapy, a chemotherapy, a surgical resection, a laparoscopic surgery and an immunotherapy, and the pharmaceutical composition is administered in one of two ways: once per two days for at least 14 days and once per day for at least 7 days.

6. The method according to claim 5, wherein the CTGF is a recombinant CTGF and/or the active fragment of CTGF is one selected from the group consisting of a C-terminal (CT) domain, a mutant of the CT domain, an active fragment of the recombinant CTGF and a combination thereof.

7. The method according to claim 5, wherein the patient is a mammal.

8. The method according to claim 7, wherein the mammal is one of a rodent and a human.

9. The method according to claim 8, wherein the amount of the CTGF administered to the rodent is 1.5 mg/kg.

10. The method according to claim 5, wherein the pharmaceutical composition further comprises a pharmaceutically acceptable carrier.

11. The method according to claim 5, wherein the pharmaceutical composition is administered to the patient via a route of administration being an intraperitoneal injection.

12. The method according to claim 5, wherein the pharmaceutical composition acts on the cancer cell of the patient.

13. The method according to claim 4, wherein the amount of the CTGF administered to the rodent is 1.5 mg/kg.

14. The method according to claim 1, wherein the pharmaceutical composition further comprises a pharmaceutically acceptable carrier.

15. The method according to claim 1, wherein the pharmaceutical composition is administered to the patient via a route of administration being an intraperitoneal injection.

16. The method according to claim 1, wherein the pharmaceutical composition acts on the cancer cell of the patient.

* * * * *